US011029300B2

(12) United States Patent
Azpiroz et al.

(10) Patent No.: US 11,029,300 B2
(45) Date of Patent: Jun. 8, 2021

(54) DETECTING CONTAMINATION SOURCES IN LIQUID DISTRIBUTION SYSTEMS

(71) Applicant: International Business Machines Corporation, Armonk, NY (US)

(72) Inventors: Jaione T. Azpiroz, Rio de Janeiro (BR); Michael Engel, Rio de Janeiro (BR); Ademir Ferreira Da Silva, Sao Paulo (BR); Ricardo L. Ohta, Sao Paulo (BR); Andre De Oliveira Botelho, Sao Paulo (BR); Mathias B. Steiner, Rio de Janeiro (BR)

(73) Assignee: International Business Machines Corporation, Armonk, NY (US)

( * ) Notice: Subject to any disclaimer, the term of this patent is extended or adjusted under 35 U.S.C. 154(b) by 327 days.

(21) Appl. No.: 16/008,303

(22) Filed: Jun. 14, 2018

(65) Prior Publication Data

US 2019/0383783 A1    Dec. 19, 2019

(51) Int. Cl.
*G01N 33/18*     (2006.01)
*G06N 7/00*      (2006.01)
(Continued)

(52) U.S. Cl.
CPC ........... *G01N 33/18* (2013.01); *G01N 21/251* (2013.01); *G01N 21/645* (2013.01); *G06F 16/29* (2019.01); *G06N 7/005* (2013.01); *G08B 21/12* (2013.01)

(58) Field of Classification Search
CPC .... G01N 33/18; G01N 21/251; G01N 21/645; G06F 16/29; G08B 21/12
See application file for complete search history.

(56) References Cited

U.S. PATENT DOCUMENTS 7,454,295 B2 * 11/2008 Wolfe .................... G01N 33/18
                                              702/22
9,528,935 B2    12/2016 Pulyassary
(Continued)

OTHER PUBLICATIONS

Peter Mell et al., "The NIST Definition of Cloud Computing". Special Publication 800-145. NIST. Sep. 2011, pp. 1-7.
(Continued)

*Primary Examiner* — Regis J Betsch
*Assistant Examiner* — Jeremy A Delozier
(74) *Attorney, Agent, or Firm* — Joseph Petrokaitis; Otterstedt, Wallace & Kammer, LLP

(57) ABSTRACT

A method and system for receiving, at a sampling location recommendation module, conventional and complementary information regarding a liquid distribution system, wherein the complementary information includes at least one of a social media post or a consumer report; processing the complementary information and a database of the liquid distribution system in the sampling location recommendation module, using computational and artificial intelligence algorithms, to generate a list of locations for sampling the liquid distribution system; displaying the list of locations; receiving a geo-tagged test record indicative of a sampled contaminant concentration value of at least one location of the list of locations; processing the geo-tagged test record, at a contamination source mapping module, to estimate a location and risk of a contamination source in the liquid distribution system; and displaying the estimated location and risk of the contamination source by modifying a map of the liquid distribution system.

19 Claims, 16 Drawing Sheets

(51) Int. Cl.
*G01N 21/25* (2006.01)
*G01N 21/64* (2006.01)
*G08B 21/12* (2006.01)
*G06F 16/29* (2019.01)

(56) References Cited

U.S. PATENT DOCUMENTS

| | | | |
|---|---|---|---|
| 2013/0073388 A1* | 3/2013 | Heath | G06Q 30/02 705/14.53 |
| 2014/0358843 A1 | 12/2014 | Subramaniam et al. | |
| 2015/0100345 A1* | 4/2015 | Holmes | G16H 50/80 705/2 |
| 2015/0355090 A1 | 12/2015 | Boday et al. | |
| 2015/0355156 A1 | 12/2015 | Boday et al. | |
| 2016/0069743 A1* | 3/2016 | McQuilkin | A22B 5/007 356/416 |
| 2017/0045628 A1 | 2/2017 | Buesseler | |
| 2018/0322941 A1* | 11/2018 | Krishnan | G01N 33/53 |

OTHER PUBLICATIONS

John E. Kelly III, "Computing, cognition, and the future of knowing", IBM Corp. Oct. 2015. pp. 1-7.
Steve Allgeier et al., "Water Security Initiative: Cincinnati Pilot Post-Implementation System Status". EPA. Sep. 2008. pp. 1-135.
I. Montalvo Arango et al., "Driving online simulations in water distribution systems", Procedia Engineering 70. Jan. 2014. pp. 1183-1191.
Mathias Braun et al., "Computational fluid dynamics modeling of contaminant mixing at junctions for an online security management toolkit in water distribution networks", Journal of Water Supply: Research and Technology—AQUA 64.5. Aug. 2015. pp. 504-515.
Nicolas Cheifetz et al., "An Incremental Sensor Placement Optimization in a Large Real-World Water System", Procedia Engineering 119. Jan. 2015. pp. 947-952.
Diogo M. Costa et al., "Localization of Contamination Sources in a Drinking Water Distribution System: A Method Based on the Residence Time of Water in Pipes". Chempor 2011: The 11th International Chemical and Biological Engineering Conference, Caparica, Portugal, Sep. 5 and 7, 2011 pp. 1-2.
Endetec, Inc., "KAPTA™ In-line Multi-parameter Water Sensors", http://www.endetec.com/en/products/kapta. Nov. 2017. pp. 1-3.
General Electric, Inc., "Industrial Water Treatment Monitoring: Chapter 36: Monitoring and Control of Water Treatment", https://www.suezwatertechnologies.com/handbook/chemical_feed_control/ch_36_monitoring.jsp. Jun. 2018. pp. 1-7.
John S. Hall et al., "Distribution System Water Quality Monitoring: Sensor Technology Evaluation Methodology and Results". EPA. Oct. 2009. pp. 1-60.
Nelson Mix et al., "Water Security Initiative: Evaluation of the Customer Complaint Surveillance Component of the Cincinnati Contamination Warning System Pilot", EPA. Apr. 2014. pp. 1-101.
Olivier Piller et al., "Installing Fixed Sensors for Double Calibration and Early-warning Detection Purposes", Procedia Engineering 119. Jan. 2015. pp. 564-572.
Marco Propato et al., "Linear Algebra and Minimum Relative Entropy to Investigate Contamination Events in Drinking Water Systems" Journal of Water Resources Planning and Management. ASCE. Jul. 2010. p. 483.
Telog, Inc., "Automated Wireless Monitoring of Water Distribution Systems". Mar. 2014. pp. 1-14.
Sandia National Laboratories, "TEVA-SPOT Toolkit: A Sensor Placement Optimization Tool for Water Security". Mar. 2013. p. 1.
Katie A. Umberg et al. "Water Security Initiative: Evaluation of the Water Quality Monitoring Component of the Cincinnati Contamination Warning System Pilot". EPA. Apr. 2014. pp. 1-118.
Hervé Ung et al., "Inverse Transport Method for Determination of Potential Contamination Sources with a Stochastic Framework". In World Environmental and Water Resources Congress 2013: Showcasing the Future. May 2013. pp. 798-812.
Hervé Ung et al., "Lessons Learned in Solving the Contaminant Source Identification in an Online Context", CUNY Academic Works. Aug. 2014. pp. 1-6.

* cited by examiner

700

{
   "Sensor Identification" : 123456,
   "Latitude" : -22.967719,        ← 701
   "Longitude" : -43.184617,
   "Contaminant Concentration" : 2.1e-6  ← 702
}

| Element ID | Type | Group | Function | Physical Characteristics | | | | | |
|---|---|---|---|---|---|---|---|---|---|
| | | | | material | Capacity (m³/h) | Pressure (kPa) | Longitude | latitude | altitude |
| 1 | Node | G1 | Valve | copper | 1000 | 50 | -22.965368 | -43.190475 | 18.2528 |
| 2 | Node | G1 | junction | pvc | 800 | 40 | -22.964464 | -43.184177 | 9.3251 |
| 3 | Node | G1 | pump | steel | 900 | 40 | -22.968074 | -43.183951 | 8.4848 |
| 4 | Node | G1 | junction | pvc | 800 | 40 | -22.968060 | -43.187824 | 9.4725 |
| ⋮ | | | | | | | | | |
| 21 | Node | G5 | hydrant | steel | 300 | 20 | -22.974949 | -43.187943 | 3.8462 |

| Element ID | Type | Group | System | Physical Characteristics | | | | |
|---|---|---|---|---|---|---|---|---|
| | | | | material | Diameter (m) | Pressure (kPa) | Length (m) | Start Node | End Node |
| A | Link | G1 | Loop | pvc | 1.2 | 30 | 154 | 1 | 2 |
| B | Link | G1 | Loop | pvc | 1.3 | 30 | 210 | 2 | 3 |
| ⋮ | | | | | | | | | |
| F | Link | NA | Bridge | copper | 2 | 80 | 424 | 5 | 6 |
| ⋮ | | | | | | | | | |
| N4 | Link | G5 | Branched | steel | 0.7 | 10 | 39 | 18 | 20 |

*FIG. 8A*

DETECTING CONTAMINATION SOURCES IN LIQUID DISTRIBUTION SYSTEMS

BACKGROUND

The present invention relates to environmental science, and more specifically, to detecting sources of contamination in liquid distribution systems.

One exemplary type of liquid distribution system is a water distribution system. Water distribution systems are large and complex networks of pipes, reservoirs, tanks, pumps, treatment plants and other components used to supply clean water to consumers. Water treatment plants monitor water quality in real time to control treatment process operations using a static network of sensors that perform water quality tests. Water quality tests include conductivity (directly related to the concentration and mobility of dissolved ions), pH, corrosion rate, turbidity, dissolved oxygen, sodium, in addition to the standard flow rate, pressure, and temperature. Some water distribution systems also include networks of sensors located at fixed locations in the distribution system, which can be used to identify anomalies outside the treatment plants.

Another exemplary type of liquid distribution system is an oil pipeline, which may include valves, branch lines, bypasses, sampling stations, etc.

SUMMARY

Principles of the invention provide techniques for detecting sources of water contamination. Generally, aspects of the invention provide a cloud computing based solution for identifying and assessing contamination events and determining the contamination source in a liquid distribution system using minimum necessary measurements at optimized locations, employing "point of analysis" (PoA) devices and leveraging "internet of things" (IoT) infrastructure. The inventive solution augments the use of conventional technology (e.g., static sensor network, customer reports) with the use of complementary technology (e.g., social media, crowdsensing, weather reports, mobile sensor network) for contamination assessment and detection in a liquid distribution system, employing portable PoA test devices and a mobile phone app or reader device. The reader or mobile device is connected to a cloud application that enables access to sources of conventional information (e.g., static sensor network), complementary information (e.g., social media, weather conditions, incident reports) and computational and artificial intelligence methods to determine optimum sampling locations. In one or more embodiments, the computational and artificial intelligence algorithms include at least one of natural language processing, image and video processing, crowdsensing data processing, computational fluid dynamics, optimization routines and statistics. Responsive to the data from the test devices and to the conventional plus complementary sources of information, the cloud application can estimate locations of source(s) of contamination in the liquid distribution system.

For example, one or more embodiments relate to a system and method for monitoring metal pipes with internal defects such as corrosive wear. As liquid flows within a faulty pipe, the liquid will be contaminated with corrosion residues. By analyzing conventional sources of information regarding the status of the water distribution system (e.g., static sensor networks) and monitoring sources of complementary information (e.g., social media, weather conditions, incident reports) in order to dynamically optimize the sampling locations where to evaluate for metal in the flowing liquid by means of the mobile network of PoA devices, it is possible to estimate in which branch of the pipe system is the internal defect.

As another example, one or more embodiments relate to a system and method for inspecting for sources of contamination in a water distribution system, such as municipal piping, a canal irrigation system, or a watershed. By continuously gathering and analyzing sources of conventional and complementary information and dynamically adjusting the location where to sample for contaminants within the water distribution system using the mobile network of PoA devices, it is possible to estimate where contaminants have entered the water distribution system. In addition, the rapid response and possible customization of the portable test devices enable prompt reaction to potential threats.

In one aspect, an exemplary method includes receiving, at a sampling location recommendation module, conventional and complementary information regarding a liquid distribution system, wherein the complementary information includes at least one of a social media post or a consumer report; processing the complementary information and a database of the liquid distribution system in the sampling location recommendation module, using computational and artificial intelligence algorithms, to generate a list of locations for sampling the liquid distribution system; displaying the list of locations; receiving a geo-tagged test record indicative of a sampled contaminant concentration value of at least one location of the list of locations; processing the geo-tagged test record, at a contamination source mapping module, to estimate a location and risk of a contamination source in the liquid distribution system; and displaying the estimated location and risk of the contamination source by modifying a map of the liquid distribution system.

One or more embodiments of the invention or elements thereof can be implemented in the form of a computer program product including a computer readable storage medium with computer usable program code for facilitating the method steps indicated. Furthermore, one or more embodiments of the invention or elements thereof can be implemented in the form of a system (or apparatus) including a memory, and at least one processor that is coupled to the memory and operative to facilitate exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a tangible computer readable storage medium (or multiple such media) and implemented on a hardware processor, or (iii) a combination of (i) and (ii); any of (i)-(iii) implement the specific techniques set forth herein.

Furthermore, a system according to an exemplary aspect of the invention includes a memory embodying computer executable instructions; at least one processor, coupled to the memory, and operative by the computer executable instructions to facilitate the method steps described above; a microfluidic device capable of carrying out a rapid chemical test and displaying an output based on a result of the test; and a mobile device with an input interface for detecting the output of the microfluidic device, the mobile device being configured to implement a mobile application that generates the geo-tagged test record by capturing and interpreting the output of the microfluidic device and combining the output of the microfluidic device with a location of the mobile device.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

In view of the foregoing, techniques of the present invention can provide substantial beneficial technical effects. For example, one or more embodiments provide one or more of:

Rapid location of water system contamination sources.

Location of water system contamination sources with enhanced precision and accuracy compared to conventional techniques.

A cloud computing based solution for continuous monitoring of information from system of records (e.g., data gathered from static and mobile sensors network) and information from system of engagement (e.g., social network) and jointly analyze using computational and artificial intelligence methods for identifying potential contamination events and determine optimum sampling locations.

A cloud computing based solution for continuous monitoring of data collected by portable point of analysis (PoA) test devices (including test results, geographical location of sample collection) and for jointly analyzing collected data with state of the art models of the water distribution system to estimate origin of contamination event.

A cloud computing based solution to apply computational and artificial intelligence techniques over collected data and to issue warnings on vulnerable sections, thereby enabling maintenance team to minimize damage and response time.

These and other features and advantages of the present invention will become apparent from the following detailed description of illustrative embodiments thereof, which is to be read in connection with the accompanying drawings.

BRIEF DESCRIPTION OF THE DRAWINGS

FIG. 7 depicts a test record utilized by the application of FIG. 3, according to an exemplary embodiment;

DETAILED DESCRIPTION

Figure 1:
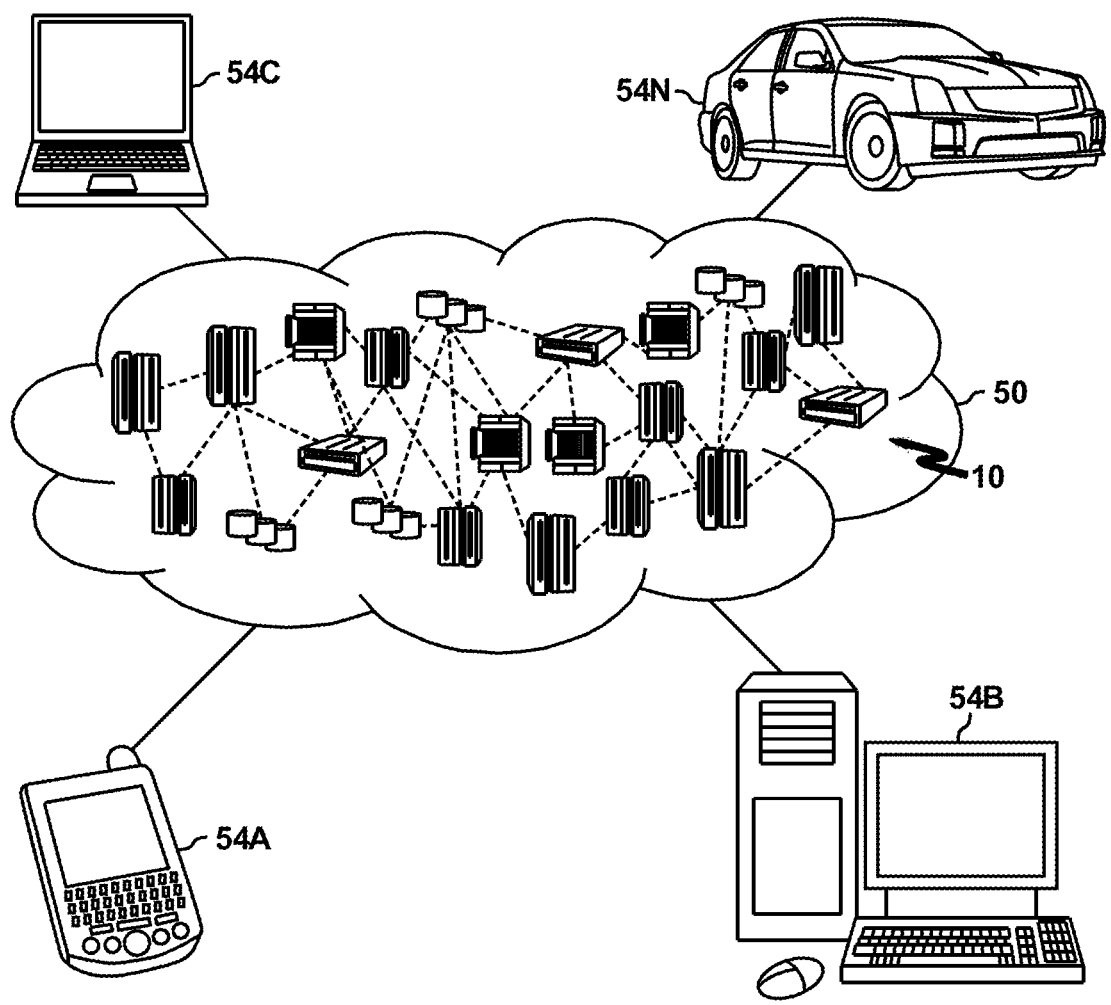
FIG. 1 depicts a cloud computing environment according to an embodiment of the present invention.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
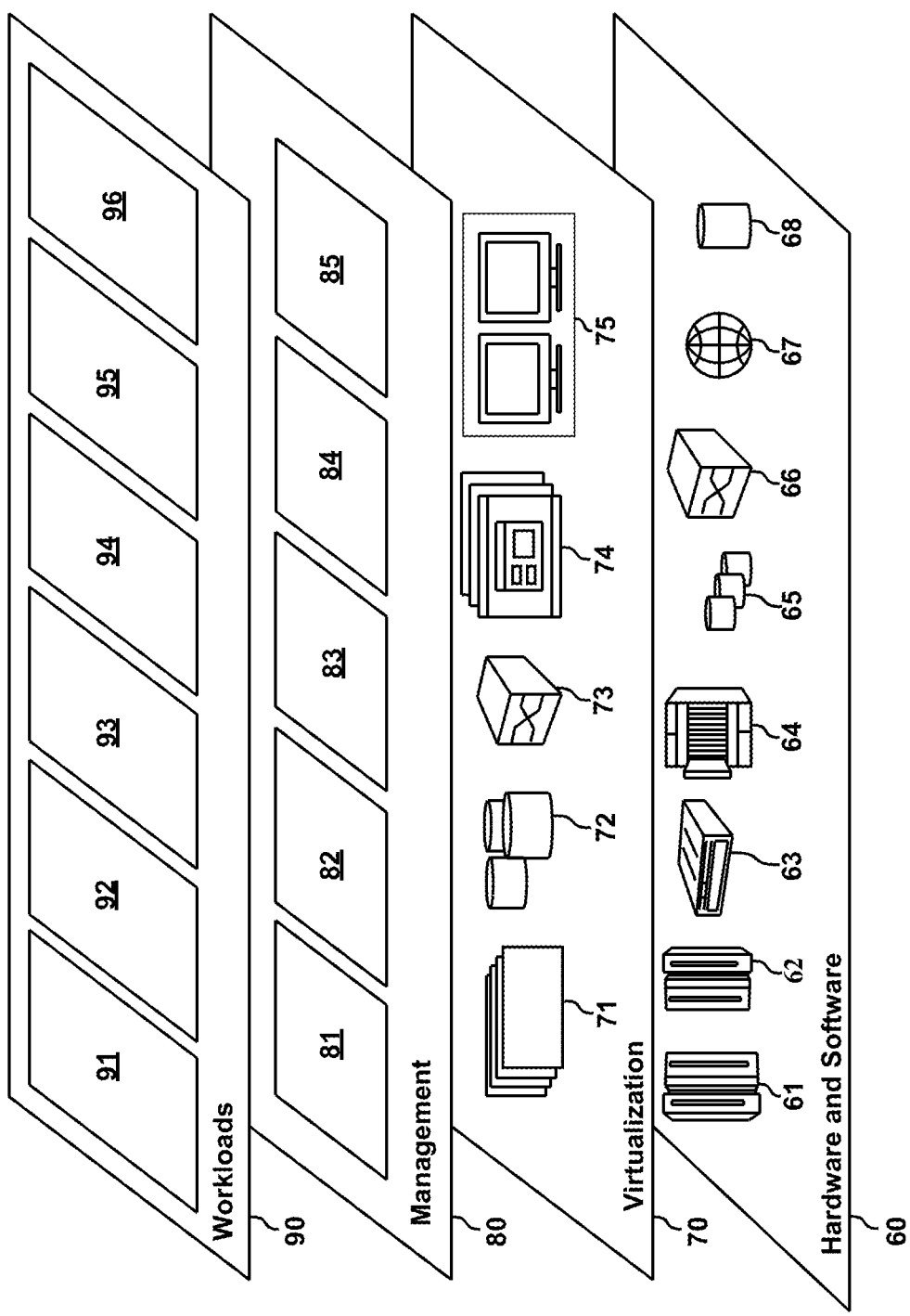
FIG. 2 depicts abstraction model layers according to an embodiment of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and an application 96 for interpreting sensor data and complementary information to generate efficient sampling locations and estimate locations of sources of water contamination. In one or more embodiments, at least a portion of the application 96 is implemented with a cognitive/artificial intelligence neural network.

Generally, an artificial intelligence (AI) neural network includes a plurality of computer processors that are configured to work together to implement one or more machine learning algorithms. The implementation may be synchronous or asynchronous. In a neural network, the processors simulate thousands or millions of neurons, which are connected by axons and synapses. Each connection is enforcing, inhibitory, or neutral in its effect on the activation state of connected neural units. Each individual neural unit has a summation function which combines the values of all its inputs together. In some implementations, there is a threshold function or limiting function on at least some connections and/or on at least some neural units, such that the signal must surpass the limit before propagating to other neurons. An AI neural network can implement supervised, unsupervised, or semi-supervised machine learning.

The application 96 is intended to be used with mobile sensor readings and other information that is complementary to the data obtained from stationary sensor stations in conventional water distribution systems. Stationary sensor stations, which are provided in main distribution lines, lack flexibility for dynamic data collection, especially in remote areas or at specific consumer sites. In order for an anomaly to be detected, the anomaly must be upstream of a sensor station. Flow rates and diffusion rates in flow can incur delays between the occurrence of an anomaly and its detection by a distant downstream station. Furthermore, anomalies that occur downstream of a sensor station (e.g., in a branch line) are not detected.

Conventional stationary sensor stations monitor only a few water quality parameters, for example, chlorine residue, pH, redox potential, turbidity, conductivity, and temperature. None of these parameters indicates the presence of specific contaminants, such as trace metals or organic chemicals. In order to detect specific contaminants in conventional water distribution systems, water samples must be collected, transported, and analyzed using bulky and expensive laboratory equipment.

Recent technological developments have enabled on-site analysis of water samples. For example, paper-based microfluidics devices provide a cost-effective approach for field tests, allowing several chemical parameters to be tested, at the same time, in a few minutes. Combined with a portable analysis device, such as a mobile device with a suitable application or a handheld analysis device, with wireless network connection (e.g., 3G/4G/Wi-Fi Internet connection) allows this test to be uploaded to a cloud-based platform, which will aggregate and provide further insights.

One or more embodiments combine prompt on-site analysis for contaminants (e.g., trace metal) with geolocation of the sample site (e.g., using an ultraviolet light sensor connected in communication with a GPS-enabled device, such as a smartphone) on a map of a water distribution system. These embodiments of the disclosure enable near-real-time detection and location of anomalous conditions in the water distribution system.

Even with the ability to analyze samples on-site, however, there still is a problem of how to determine where and when to sample the water. Granular, routine sampling is intrusive on consumers, time consuming, labor intensive and expensive to implement. Randomized and sporadic sampling is less intrusive and less expensive, but also less effective for identifying anomalies. One or more embodiments resolve this problem by generating a list of locations for sampling to be implemented, responsive to complementary information such as social media posts, weather conditions, or incident reports.

Figure 3:
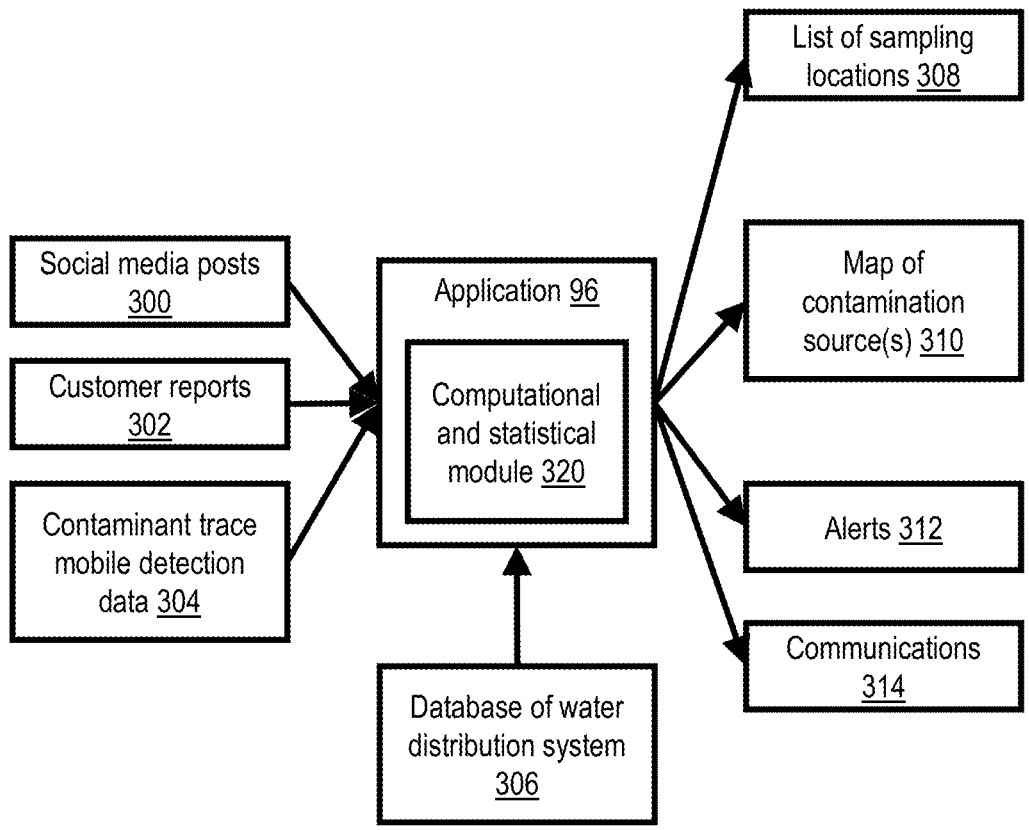
FIG. 3 depicts operation of an application for interpreting sensor data and complementary information to generate efficient sampling locations and estimate locations of sources of water contamination, according to an exemplary embodiment.

FIG. 3 depicts the operation of an embodiment of the inventive application 96. The application 96 is applicable to municipal water systems, oil pipelines, natural water flows, and other liquid distribution systems, and may operate in combination with conventional sources of information regarding the liquid distribution system (e.g. data from static network of water quality sensors) and conventional methods of processing conventional sources of information of liquid distribution system. In the following, it is understood that data from conventional sources of information and methods to process that data are available and the description refers to the inventive components of the application related to the processing of complementary sources of information regarding the liquid distribution systems. In one or more embodiments, the application 96 integrates and fuses real time data including social media posts 300 (e.g., consumer complaints regarding quality of municipal water supply), customer reports 302 from dedicated apps (i.e., crowdsensing), and, when available, contaminant trace detection data 304 on liquid samples from one or more portable measurement systems that provide geo-referencing of sampling locations. The application 96 leverages a geographic layout database 306 of the liquid distribution system (e.g., a municipal water supply network), and uses state-of-the-art computational algorithms for hydraulic modelling and simulation of a water distribution system (see, for example, "Computational Fluid Dynamics Modeling of Contaminant Mixing at Junctions for an online Security Management Toolkit in Water Distribution Networks", Journal of Water Supply: Research and Technology-AQUA, IWA, 64(5), 504-515 (2015). DOI: 10.2166/aqua.2015.066; Montalvo Arango I. and Deuerlein J., "Driving Online Simulations in Water Distribution Systems", Procedia Engineering, 70(0), 1183-1191, DOI: 10.1016/j.proeng.2014.02.131), and for optimal sensor allocation (see, for example, "An Incremental Sensor Placement Optimization in a Large Real-World Water System". Nicolas Cheifetz et. al. Procedia Engineering 119 (2015) 947-952. DOI: 10.1016/j.proeng.2015.08.977; "Installing Fixed Sensors for Double Calibration and Early-warning Detection Purposes", Procedia Engineering, 119, 564-572. DOI: 10.1016/j.proeng.2015.08.909.; "A Sensor Placement Optimization Tool for Water Security. Sandia National Laboratories. https://software.sandia.gov/trac/spot). The application 96 uses statistical methods for contamination source determination (see, for example, D. E. Wagner and R. M. Neupauer, "Source Identification in Water Distribution Systems using the Adjoint Method with Non-Ideal Sensors and Non-Detect Measurements". Environmental Water Resources Congress 2013: Show casing the Future, ASCE, pp. 975-981. DOI:10.1061/9780784412947.094; Ung, H., Piller, O., Gilbert, D. & Mortazavi, I., "Inverse Transport Method for Determination of Potential Contamination Sources with a Stochastic Framework". 2013. World Environmental Water Resources Congress 2013: Showcasing the Future, ASCE, pp. 798-812, DOI: 10.1061/9780784412947.077; Ung, Hervé; Piller, Olivier A.; Jochen, Deuerlein; Gilbert, Denis; and Idel, Montalvo, "Lessons Learned In Solving The Contaminant Source Identification In An Online Context" (2014). CUNY Academic Works. http://academicworks.cuny.edu/cc_conf_hic/89). One or more of these exemplary algorithms are collected in the application 96 under a computational and statistical module 320, to produce a list 308 of suggested sampling locations, based on complementary information (e.g., social media posts and consumer reports) as well as contaminant concentration measurement data when available, for example, metal trace data as it correlates to metal released into municipal water by corroded pipes. Application 96 and the computational and statistical module 320 are further applied to the database 306, with input from the contaminant trace detection data 304 at the suggested sampling locations, to generate a map 310 of estimated locations where contaminants may be entering the system. In one or more embodiments, the map 310 visually indicates a risk or probability of a failure in various pipe sections or of an external source of contamination. Thus, based on the fused real time data 300, 302, 304 and the geographic layout database 306, the application 96 generates a list 308 of suggested sampling locations, the map 310 of estimated risks of defective pipe sections or contamination sources, and alerts 312 regarding potential weak or risky sections of piping. The alerts 312 can be, in certain embodiments, audible, visible, or electronic alerts that draw attention to a risk of a contamination source in the liquid distribution system. In one or more embodiments, the application 96 also generates paper or electronic communications 314 recommending further testing locations and/or recommending suspension of water distribution to a section suspected of contamination.

Figure 4:
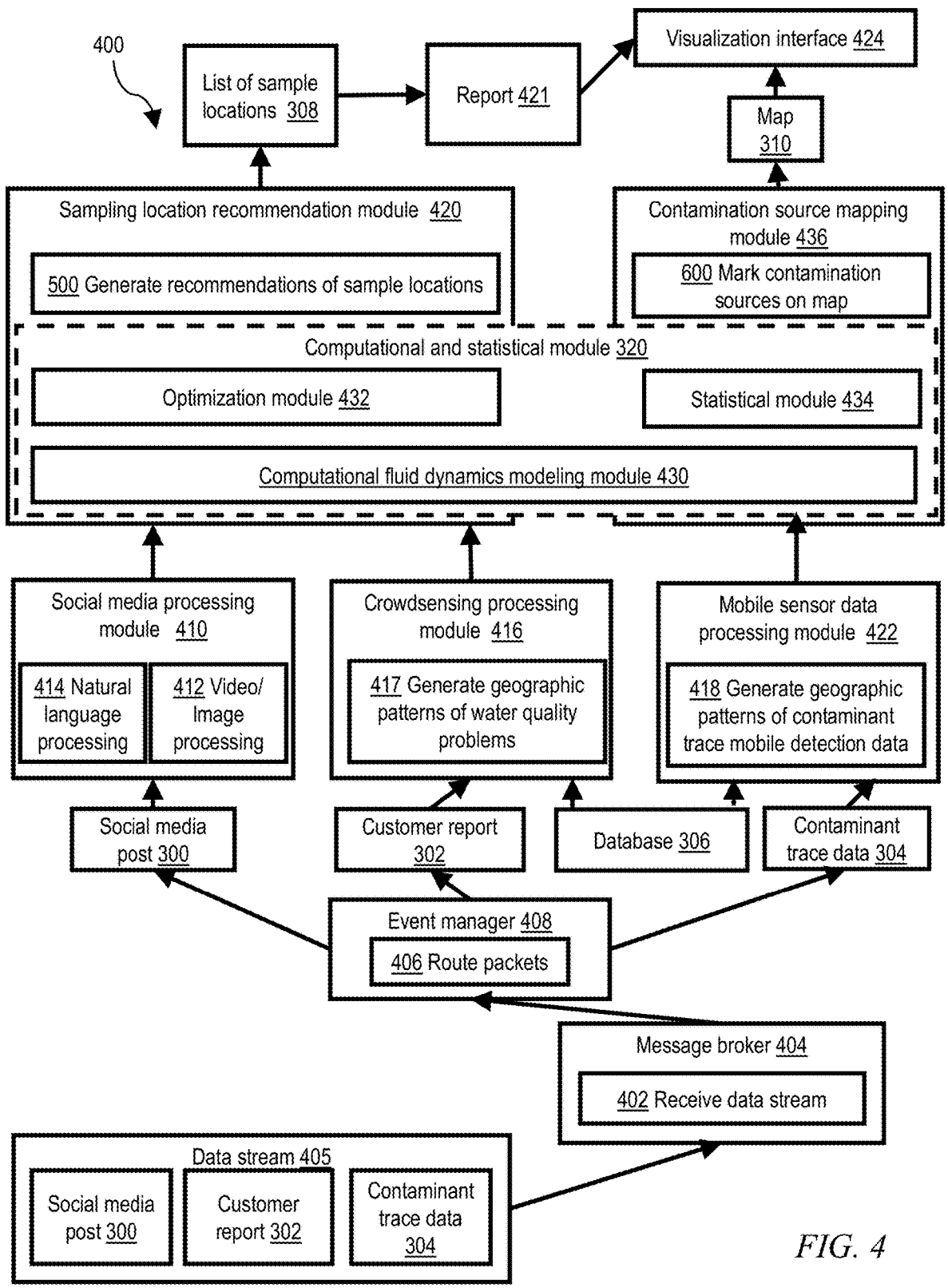
FIG. 4 depicts details of a method implemented by the application of FIG. 3, according to an exemplary embodiment.

FIG. 4 depicts details of a method 400 implemented by the application 96. At 402, a message broker 404 receives an incoming data stream 405 that includes the social media posts 300, the customer reports 302, and the geo-tagged contaminant trace mobile detection data 304. At 406, an event manager 408 routes each packet of the incoming data stream to an appropriate module of the application 96.

Figure 15:
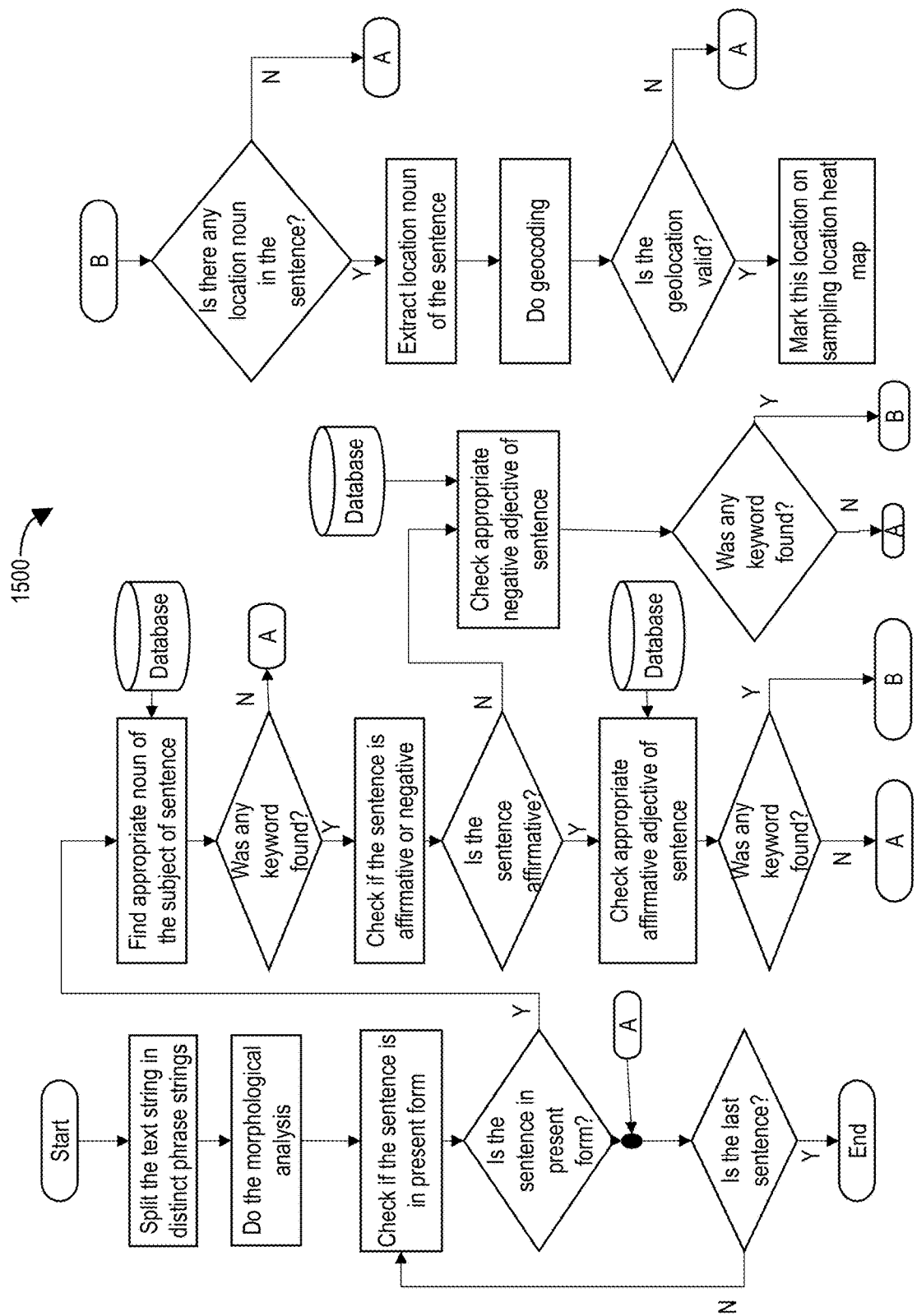
FIG. 15 depicts an exemplary natural language processing flow as implemented by the sampling location recommendation module of FIG. 5, according to an exemplary embodiment.

The event manager 408 routes the social media posts 300 to a social media processing module 410, which can be implemented using a neural network as previously mentioned. At 412 the social media processing module 410 conducts video/image processing and at 414 it conducts natural language processing on the social media posts. For example the video/image processing 412 recognizes and classifies pre-evaluated objects and colors relevant to water quality (e.g., glasses, jars, water tank, swimming pools). In one or more embodiments, the video/image processing 412 can be implemented through services, such as IBM Watson Visual Recognition service from IBM Cloud platform. The natural language processing 414 detects and classifies consumer sentiments related to water quality (e.g., taste, odor, color) and also detects discussions about events that can compromise water quality (e.g., accidents, weather events, flooding, earthquake). It can generate keywords and its citation number, which could be used to generate a priority ranking, which can be especially useful for crisis management. In one or more embodiments, the natural language processing 414 can be implemented through IBM Watson Alchemy API from IBM Cloud platform. FIG. 15 depicts an exemplary natural language processing flow 1500 as implemented by the social media processing module 410. Note with reference to FIG. 15 that an "affirmative sentence" is one that positively states a problem or deficiency, so that an "appropriate affirmative adjective" is a disparaging word or phrase, e.g., "dirty" or "turbid" or "nasty"; a "negative sentence" is one that identifies the absence of a desired quality, so that an "appropriate negative adjective" is a laudatory word or phrase, e.g., "clean" or "fresh" or "clear". Note also that a "valid" geolocation is a latitude and longitude coordinate that corresponds uniquely to the location noun. Therefore, location nouns such as "home" or "work" or "my house" only can produce valid geolocations if additional contextual data is supplied.

Referring again to FIG. 4, the social media processing module 410 also attempts to geo-tag the classified images and consumer sentiments based on detection of known buildings/constructions using, for example, structural features, if the geo-tagging picture information is not available. An exemplary implementation of this feature is described in Alex Krizhevsky, Ilya Sutskeverm, Geoffrey E. Hinton, "ImageNet classification with deep convolutional neural networks"—Proceedings of the 25th International Conference on Neural Information Processing Systems—Volume 1—Pages 1097-1105, (2012).

The event manager 408 routes the geo-tagged customer reports 302 to a crowdsensing processing module 416, which also receives the geographic layout database 306 of the liquid distribution system and at 417 compiles the reports 302 to generate geographic patterns of water quality problems. As exemplary implementation of this feature is shown in Zheng Xu, Yunhuai Liu1, Hui Zhang, Xiangfeng Luo, Lin Mei, Chuanping Hu, "Building the Multi-Modal Storytelling of Urban Emergency Events Based on Crowdsensing of Social Media Analytics"—Mobile Netw. Appl. (2017) 22:218-227, DOI: 10.1007/s11036-016-0789-2. The procedure followed for compiling the reports 302 to generate geographic patterns of water quality problems is similar to the method 600, further discussed below with reference to FIG. 6, for marking contamination sources based on the contaminant trace detection data 304.

Based on the geo-tagged social media data 300 and customer reports 302, at 500 a sampling location recommendation module 420 generates a report 421 with recommendations of sample collection locations by using input from a computational fluid dynamics modeling module 430 to perform hydraulic simulations of the water distribution system and by using an optimization module 432 to apply optimization methods for optimal sensor allocation, both within the computational and statistical module 320.

Figure 5:
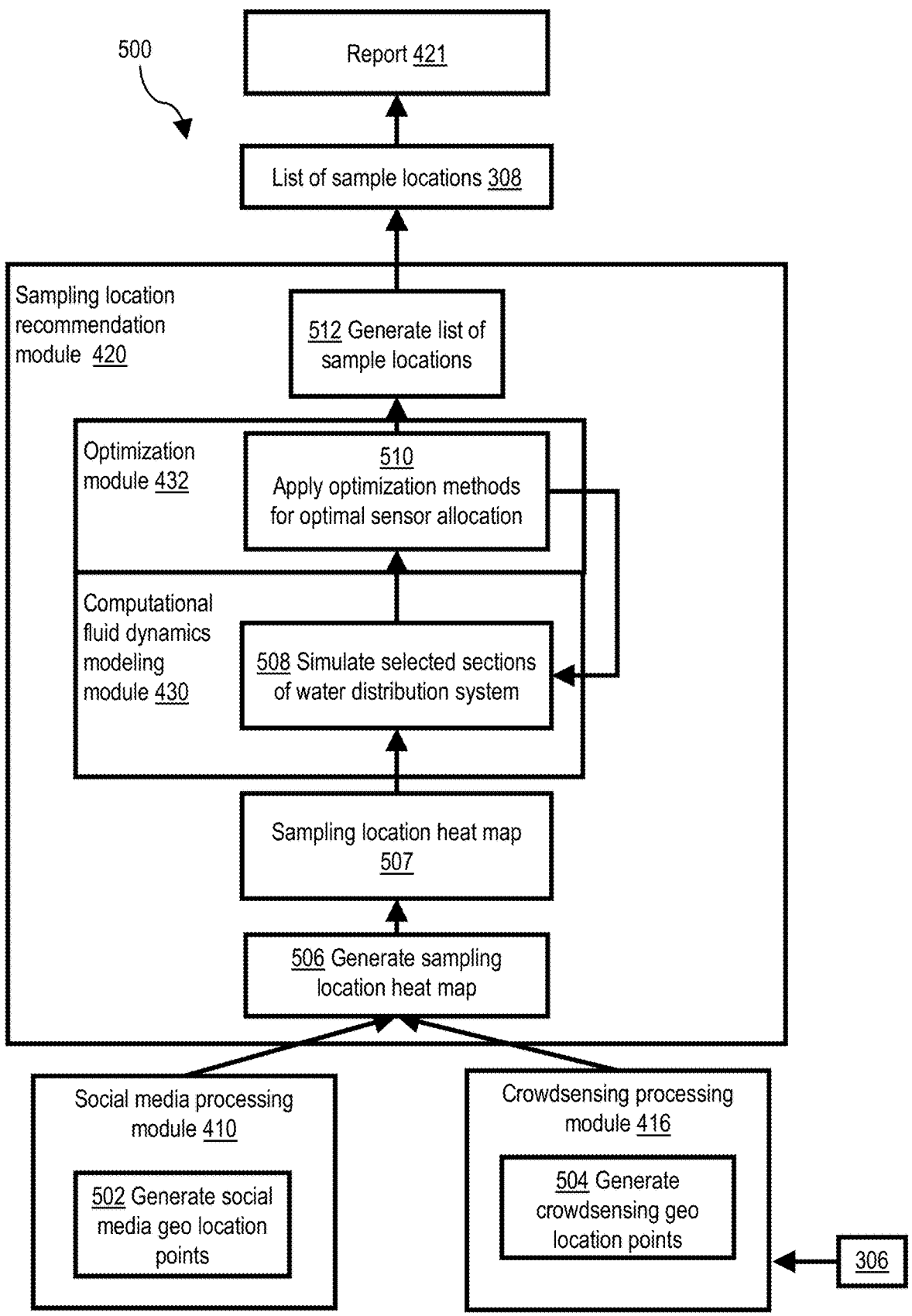
FIG. 5 depicts a method implemented by a sampling location recommendation module of the application of FIG. 4, according to an exemplary embodiment.

FIG. 5 depicts the method 500 that is implemented by the sampling location recommendation module 420. At 502 the application 96 uses social media processing module 410 to generate social media geo location points based on social media posts 300, and at 504 the application 96 uses crowdsensing processing module 416 to generate crowdsensing geo location points, based on collected customer reports 302 and the geographic layout database 306 of the liquid distribution system. Based on the social media geo location points and the crowdsensing geo location points, at 506 the application 96 generates a sampling location heat map 507 which highlights the regions where customers posted to social media or created reports as a function of perceived priority. At 508 the sampling location recommendation module 420 then simulates the fluid dynamics on selected sections of the water distribution system that are identified by the sampling location heat map 507, using the computational fluid dynamics modeling module 430. At 510 the sampling location recommendation module 420 leverages an optimization module 432 to apply optimization techniques in order to narrow down on a minimum number of sampling locations that produce the most effective probing of the system. This simulation and optimization process may be iterative. Eventually, at 512 the sampling location recommendation module 420 generates the list of sample locations 308, which is converted to report 421, suitable for visualization interface 424.

Referring again to FIG. 4, the event manager 408 routes the geo-tagged contaminant trace detection data 304 to a mobile sensor data processing module 422, which also receives the geographic layout database 306 of the liquid distribution system. At 418 the mobile sensor data processing module 422 processes the contaminant trace 304 to generate geographic patterns of contaminant trace data by creating, for example, a spatial distribution of the measured contaminant concentration in relation to the water distribution system layout 306.

Based on the contaminant trace detection data 304, at 600 a contamination source mapping module 436 leverages the computational and statistical module 320 to determine a likely location of the source of contamination in the water distribution system, using simulations from the computational fluid dynamics modeling module 430 and statistical methods from a statistical module 434. The contamination source mapping module 436 then supplies the location information to visualization interface 424 in the form of the map 310.

In one or more embodiments, the geo-tagged contaminant trace detection data 304 is produced by technology for detecting small traces of metals in water (e.g., copper, lead, arsenic) (see, e.g., U.S. Patent Publ. 2015/0355090A1, U.S. Patent Publ. 2015/0355156A1), and source of contamination sought by the algorithms include damaged or defective metallic water pipes in water distribution systems.

Figure 6:
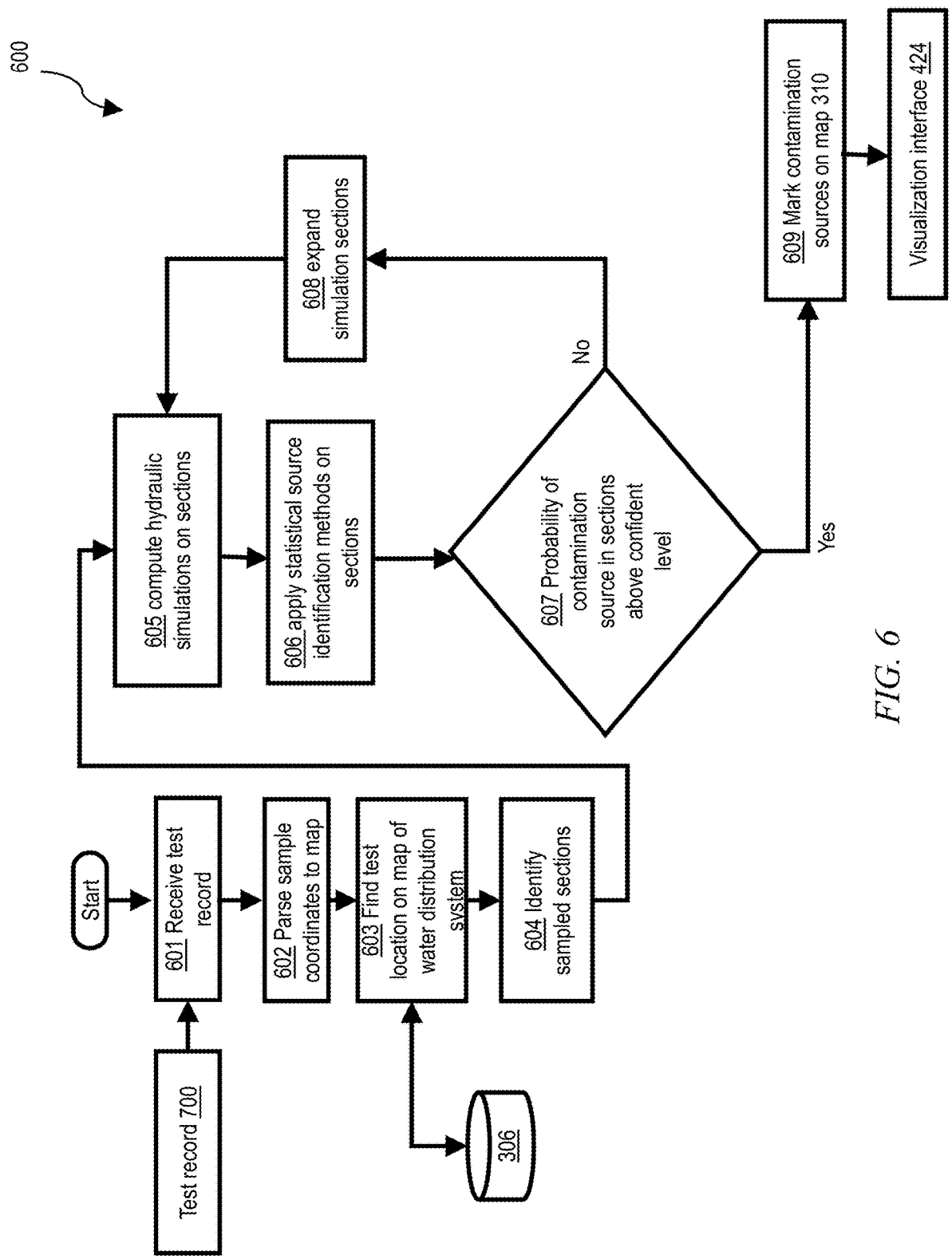
FIG. 6 depicts a method implemented by a contamination sources mapping module of the application of FIG. 4, according to an exemplary embodiment.

FIG. 6 depicts the method 600 that is implemented by the contamination source mapping module 436. At 601, receive a new test record 700 and insert the record in a test database as a new sensor measurement. FIG. 7 depicts an example of the test record 700 with reference characters corresponding to features that will be further discussed with reference to the method of FIG. 6.

Figure 8B:
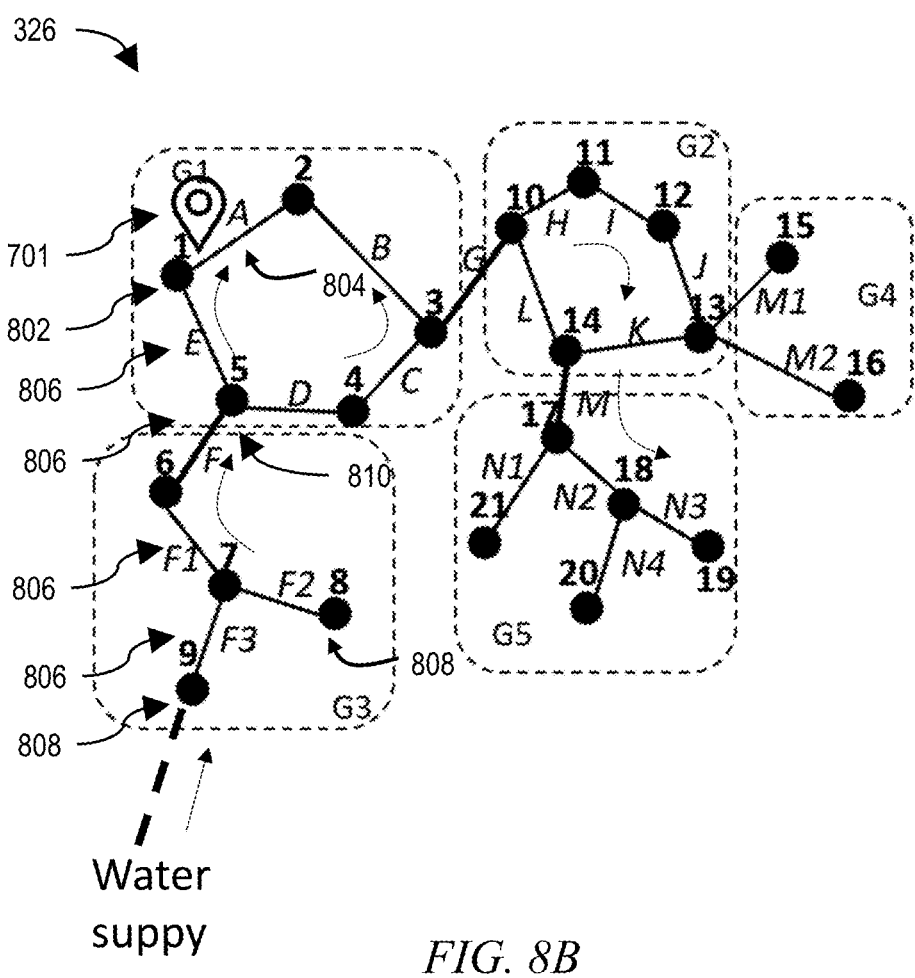
FIG. 8A depicts an exemplary database record corresponding to a water distribution system and 8B depicts a portion of a water distribution system map utilized by the application of FIG. 3, according to an exemplary embodiment.

At 602, parse sample coordinates 701 from the test record 700 in order to locate the sample on the geographic layout database 306 of the liquid distribution system. FIGS. 8A-8B depict a portion of an exemplary water distribution system database 306 consisting of a hydraulic component inventory 316 and the corresponding network visualization 326 with reference characters corresponding to features that will be further discussed with reference to the method of FIG. 6.

At 603, query the database 306 to find a component 802 of the water distribution system that is nearest to the sample coordinates 701. At 604, identify a section 804 of the water distribution system that connects to the component 802 and is being probed, and identify upstream sections 806 for simulation, for example, by evaluating a shortest path from the sampled pipe 804 to a water supply 808. For example, Dijkstra's graph traversal algorithm can be used. At 605, apply computational fluid dynamics modeling module 430 and at 606, apply statistical methods from statistics module 434, in order to determine a probability that the source of contamination is in the sampled sections 806 and an estimated location of the source of contamination. If at 607 a computed chance that the source of contamination is within the section is below a confidence level, steps 605 and 606 are repeated iteratively, expanding or adjusting the sampled sections 806 at 608, until the desired confidence level in the contamination source estimation is reached. At 609, the estimated location of the contamination sources is marked on the map 310 and transferred to visualization interface 424. Map 310 may be a modified version of the network visualization 326 of the liquid distribution system database that includes the estimated location of the contamination sources.

Referring again to FIG. 4, the sampling location recommendation module 420 forwards its report 421 with the list of suggested sample locations 308 to a visualization interface 424. Similarly, the contamination source mapping module forwards its map 310 to the visualization interface 424. One example of a visualization interface could be a combination of map visualization interface (e.g., ArcGIS) with graph visualization interface (e.g., Graphviz) and a complementary visualization library (e.g., D3.js), to provide additional data visualization features (such as bar charts, line chart, etc.), served out by a server or the like, to a browser of a computing device of a user, via a webpage. The maps interface is parsed by the browser on the user's computing device to create a graphical user interface (GUI).

Figure 9:
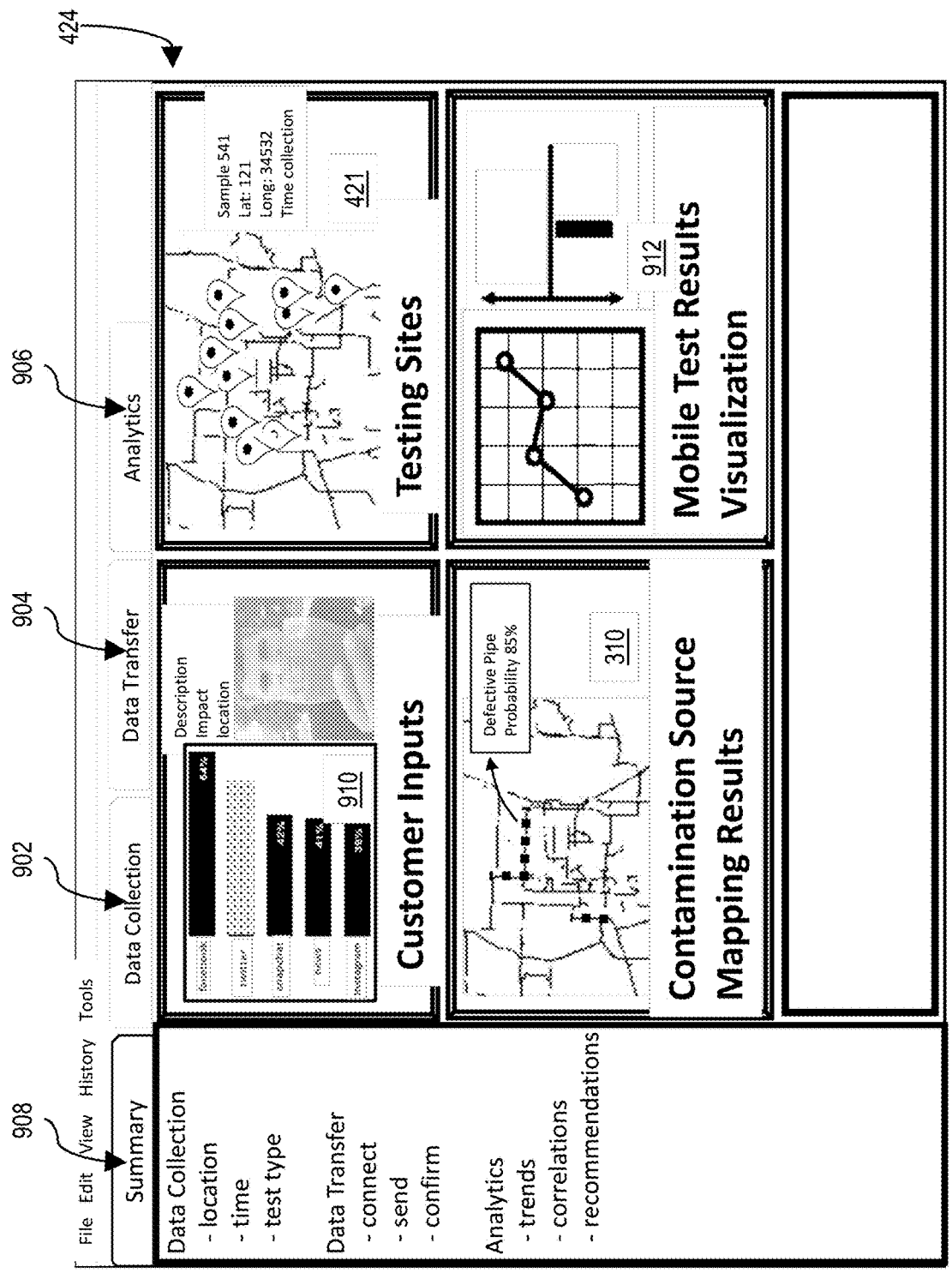
FIGS. 9-12 depict various displays of a visualization interface produced by the application of FIG. 3.

FIG. 9 depicts an exemplary display of the visualization interface 424. The visualization interface 424 includes a data collection tab 902, a data transfer tab 904, an analytics tab 906, and a summary tab 908. In FIG. 9, the summary tab 908 is selected to display the testing sites report 421 and the map of contamination source(s) 310. The summary tab 908 also displays a graphical representation 910 of sentiment data obtained from the social media posts 300 and displays a visualization 912 of sample reader results.

Figure 10:
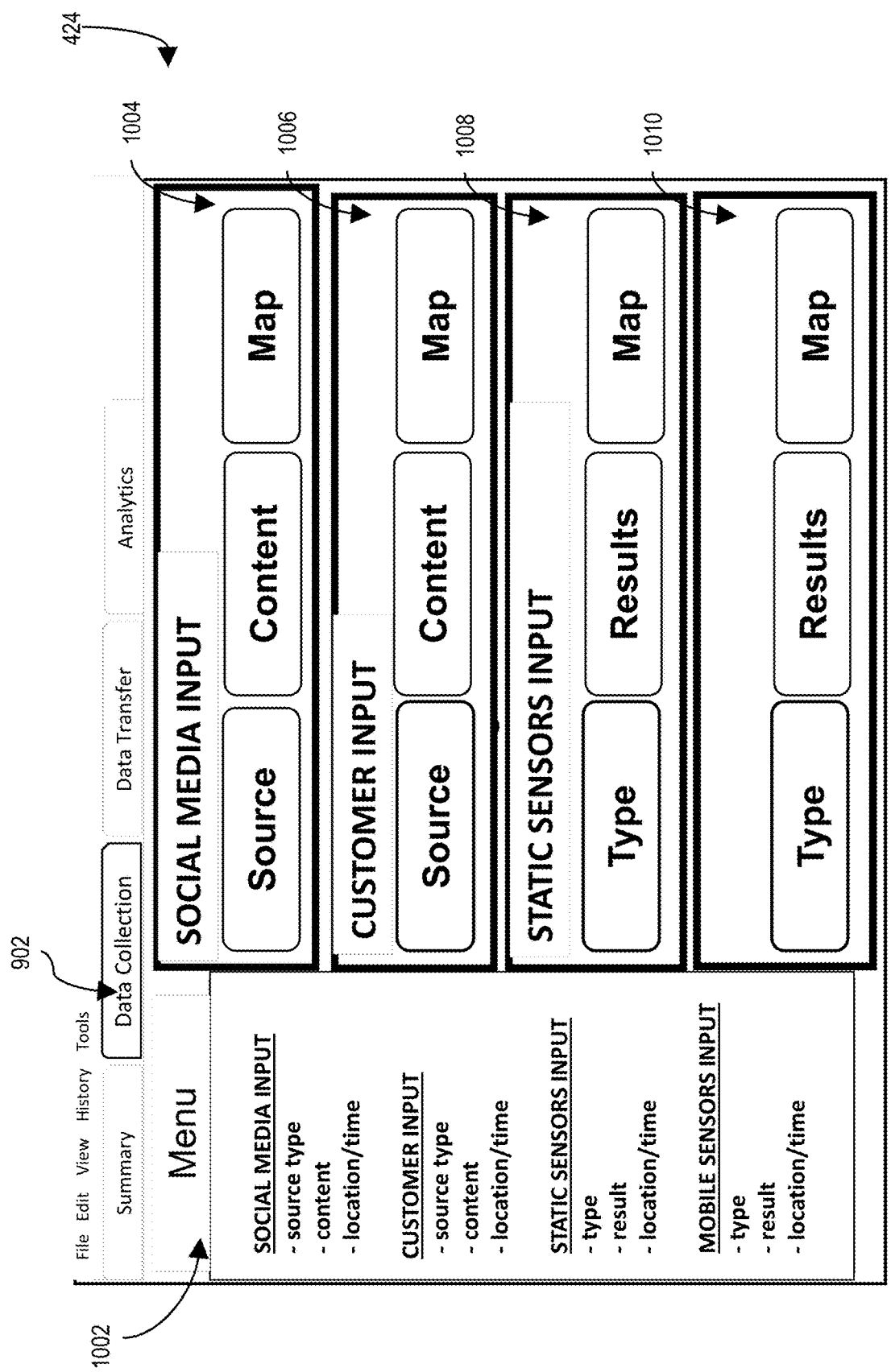

In FIG. 10, the data collection tab 902 is selected to show an example of the visualization interface containing a drop-down menu 1002 where the various functionalities can be selected or, alternatively, these functionalities can be selected by clicking on the various buttons on the screen. These functionalities may include the collection of social media input 1004, customer input 1006, static sensors input 1008 and mobile sensors input 1010, each comprising information about their source or type, content or results and location and time of collection.

Figure 11:
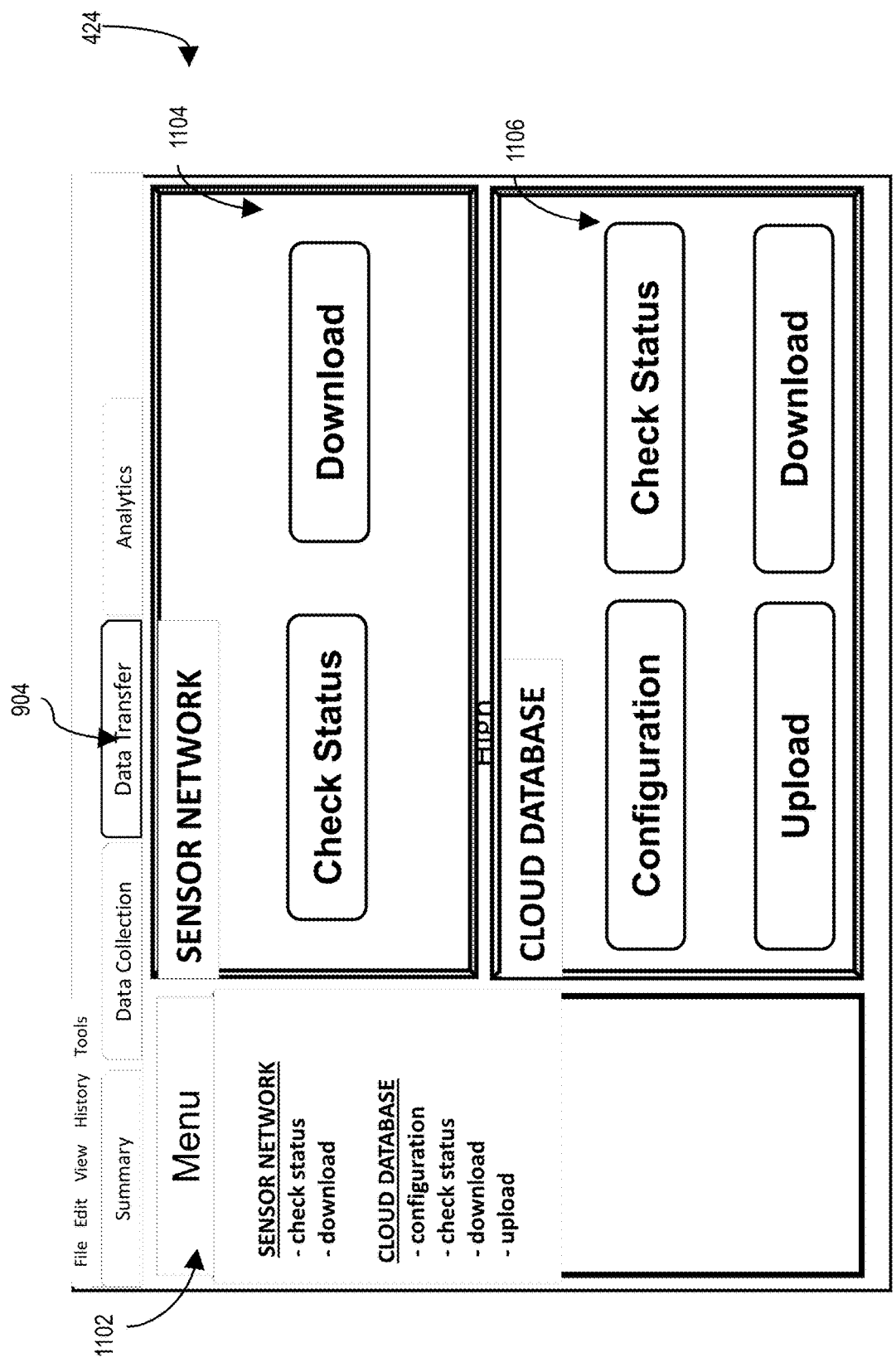

In FIG. 11, the data transfer tab 904 is selected to show an example of the visualization interface containing a drop-down menu 1102 where the various functionalities can be selected or, alternatively, these functions can be selected by clicking on the various buttons on the screen. These functionalities may include sensor network 1104 and cloud database management 1106, comprising operations such as sensor status diagnostics and data download, and cloud database communication diagnostics, data transfer and configuration (URL, instance name, API Connect configuration, etc.).

Figure 12:
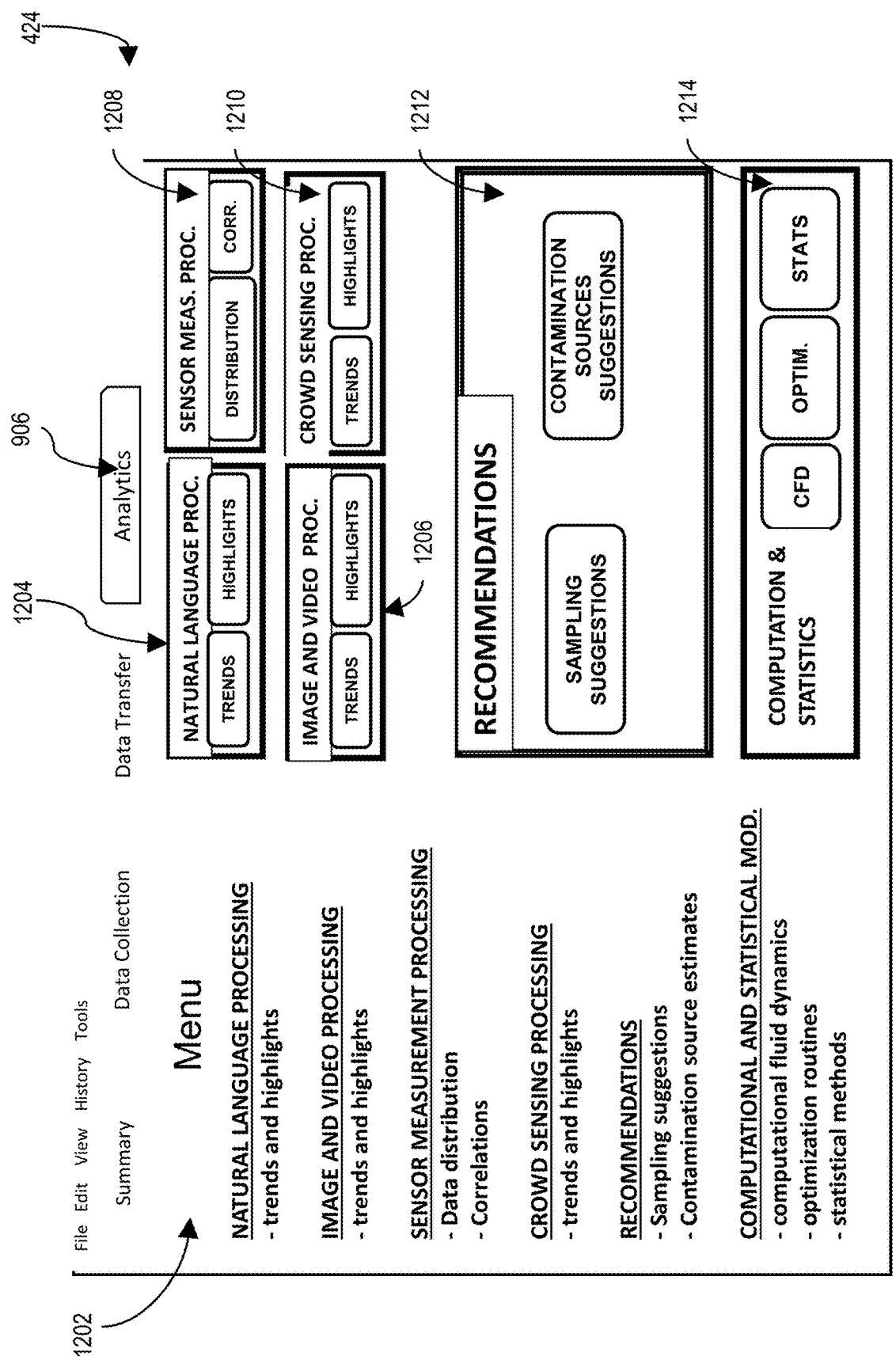

In FIG. 12, the analytics tab 906 is selected to show an example of the visualization interface containing a drop-down menu 1202 where the various functionalities can be selected or, alternatively, these functions can be selected by clicking on the various buttons on the screen. These functionalities may include natural language processing 1204, image and video processing 1206, sensor measurement processing 1208 and crowd sensing processing 1210, comprising operations such as identifying trends and highlights, or computing measurement distributions and correlations between data sources, including for instance weather data. Additional functionalities under the analytics tab 906 may include access to the computational and statistical module 320 through a user interface 1214 and a recommendations interface 1212 where to access suggested list of sampling locations and of contamination sources.

Figure 13:
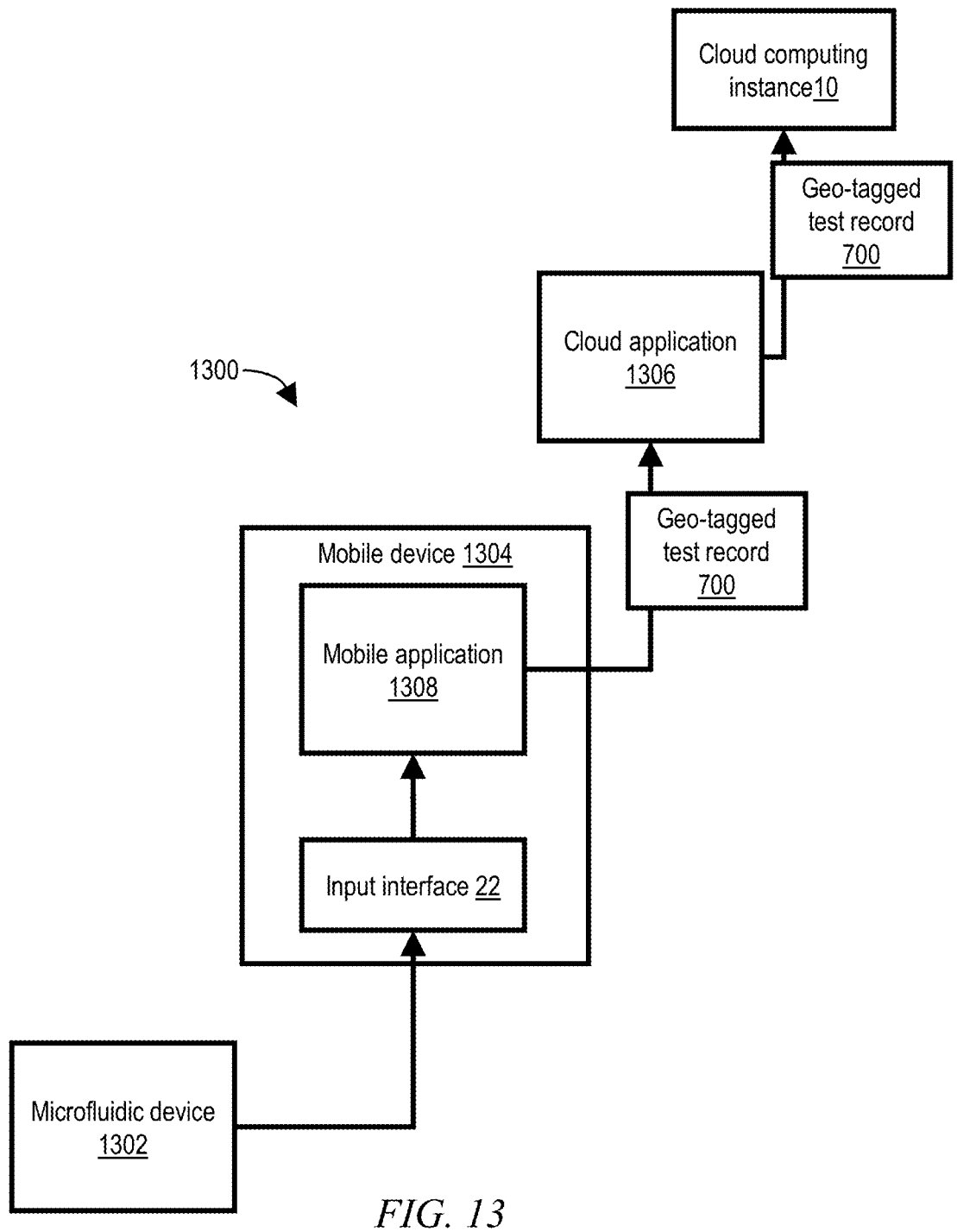
FIG. 13 depicts an exemplary apparatus for implementing the application of FIG. 3, including a computer, a microfluidic device, and a mobile device, according to an exemplary embodiment.

FIG. 13 depicts a system 1300 for implementing the application 96. The system 1300 includes a first cloud computing instance 10 (further described below with reference to FIG. 14) as well as a microfluidic device 1302 and a mobile device 1304 (including many like components to those of the first cloud computing node 10, which are further described with reference to FIG. 14). The mobile device 1304 is connected in communication with the first cloud computing node 10 via a cloud application 1306, and executes a mobile application 1308 that interacts with the microfluidic device 1302 and with the cloud application 1306. For example, the mobile application 1308 uses an input interface 22 of the mobile device 1304 (e.g., a camera) to capture output from the microfluidic device 1302, interprets the captured output, and combines the interpreted output 702 (as shown in FIG. 7) with the mobile device location 701 (as shown in FIG. 7) to generate the geo-tagged test record 700. The mobile application 1308 then transfers the geo-tagged test record 700 to the first cloud computing node 10 via the cloud application 1306.

For example, in one or more embodiments the microfluidic device 1302 is a paper-based analytical device that is capable of performing rapid chemical tests, e.g., an assay for at least one of pH, aluminum, nickel, magnesium, calcium, phosphorus, potassium, copper, lead, mercury, or antimony.

In one or more embodiments the microfluidic device 1302 produces a colorimetric output corresponding to a result of the assay, for example, a portion of the microfluidic device 1302 may darken or change in color proportional to a concentration of the assay target. In one or more embodiments the microfluidic device 1302 produces a fluorescent light in response to an ultraviolet excitation, corresponding to a result of the assay, in which the signal intensity is proportional to a concentration of the assay target.

In one or more embodiments, the first cloud computing instance 10 responds to the geo-tagged test record 700 by activating an audible, visible, or electronic alert 312 to bring attention to a risk of a contamination source; issuing a paper or electronic communication 314 recommending further testing locations; and issuing a paper or electronic communication recommending suspension of water distribution to a section suspected of contamination.

In one or more embodiments, the first cloud computing instance 10 responds to the geo-tagged test record 700 by broadcasting to the mobile device 1304 an updated location and risk of a contamination source along with an updated list of sampling locations.

Given the discussion thus far, it will be appreciated that, in general terms, an exemplary method, according to an aspect of the invention, includes receiving, at a sampling location recommendation module 420, complementary information 300, 302 regarding a liquid distribution system, wherein the complementary information includes at least one of a social media post 300 and/or a consumer report 302; processing the complementary information and a database 306 of the liquid distribution system in the sampling location recommendation module, using computational and artificial intelligence algorithms, to generate a list 308 of locations for sampling the liquid distribution system. The exemplary method further includes displaying the list of locations, e.g., via a visualization interface 424. The exemplary method further includes receiving a geo-tagged test record 700 indicative of a sampled contaminant concentration value of at least one location of the list of locations; processing the geo-tagged test record, at a contamination source mapping module 436, to estimate a location and risk of a contamination source in the liquid distribution system; and displaying the estimated location and risk of the contamination source by modifying a map 310 of the liquid distribution system.

In one or more embodiments, processing the geo-tagged test record includes 603 locating the sampled contaminant concentration value on the network visualization 326 of the liquid distribution system database by 602 parsing sample coordinates from the geo-tagged test record 700; 604 identifying sampled sections of the liquid distribution system based on a shortest path from a section nearest the sample coordinates; and 605 determining a probability that the source of contamination is in the sampled sections using hydraulic modeling of the sampled sections and statistical methods.

In one or more embodiments, the exemplary method further includes producing the geo-tagged test record by operation of a microfluidic device 1302 capable of performing rapid chemical tests. For example, the microfluidic device 1302 is a paper-based analytical device.

In one or more embodiments, the exemplary method further includes obtaining a result from the microfluidic device 1302 via a colorimetric output. In one or more embodiments, the exemplary method further includes generating the geo-tagged test record 700 by capturing and interpreting the colorimetric output from the microfluidic device 1302 via a mobile device application 1308; and transferring the geo-tagged test record to a cloud application 1306 via the mobile device application.

In one or more embodiments, the exemplary method further includes obtaining a result from the microfluidic device 1302 via a fluorescent signal, generated by an ultraviolet source. In one or more embodiments, the exemplary method further includes generating the geo-tagged test record 700 by capturing and interpreting the fluorescent signal output from the microfluidic device 1302 via a mobile device application 1308; and transferring the geo-tagged test record to a cloud application 1306 via the mobile device application.

In one or more embodiments, the microfluidic device carries out chemical tests including an assay for at least one of pH, aluminum, nickel, magnesium, calcium, phosphorus, potassium, copper, lead, mercury, or antimony.

In one or more embodiments, the computational and artificial intelligence algorithms include at least one of natural language processing, image and video processing, crowdsensing data processing, computational fluid dynamics, optimization routines and statistics.

In one or more embodiments, the exemplary method further includes activating an audible, visible, or electronic alert 312 to bring attention to the risk of the contamination source; issuing a paper or electronic communication 314 recommending further testing locations; and issuing a paper or electronic communication recommending suspension of water distribution to a section suspected of contamination.

One or more embodiments of the invention, or elements thereof, can be implemented in the form of an apparatus including a memory and at least one processor that is coupled to the memory and operative to perform exemplary method steps, or in the form of a non-transitory computer readable medium embodying computer executable instructions which when executed by a computer cause the computer to perform exemplary method steps.

For example, an exemplary apparatus includes a memory embodying computer executable instructions, and at least one processor, coupled to the memory, and operative by the computer executable instructions to facilitate any combination of the exemplary method steps described above. Further, in one or more embodiments the exemplary apparatus also includes a microfluidic device capable of carrying out a rapid chemical test and displaying an output based on the detected concentration result of the test; and a mobile device with an input interface for detecting the output of the microfluidic device, the mobile device being configured to implement a mobile application that generates a geo-tagged test record by capturing and interpreting the output of the microfluidic device and combining the output of the microfluidic device with a location of the mobile device.

Figure 14:
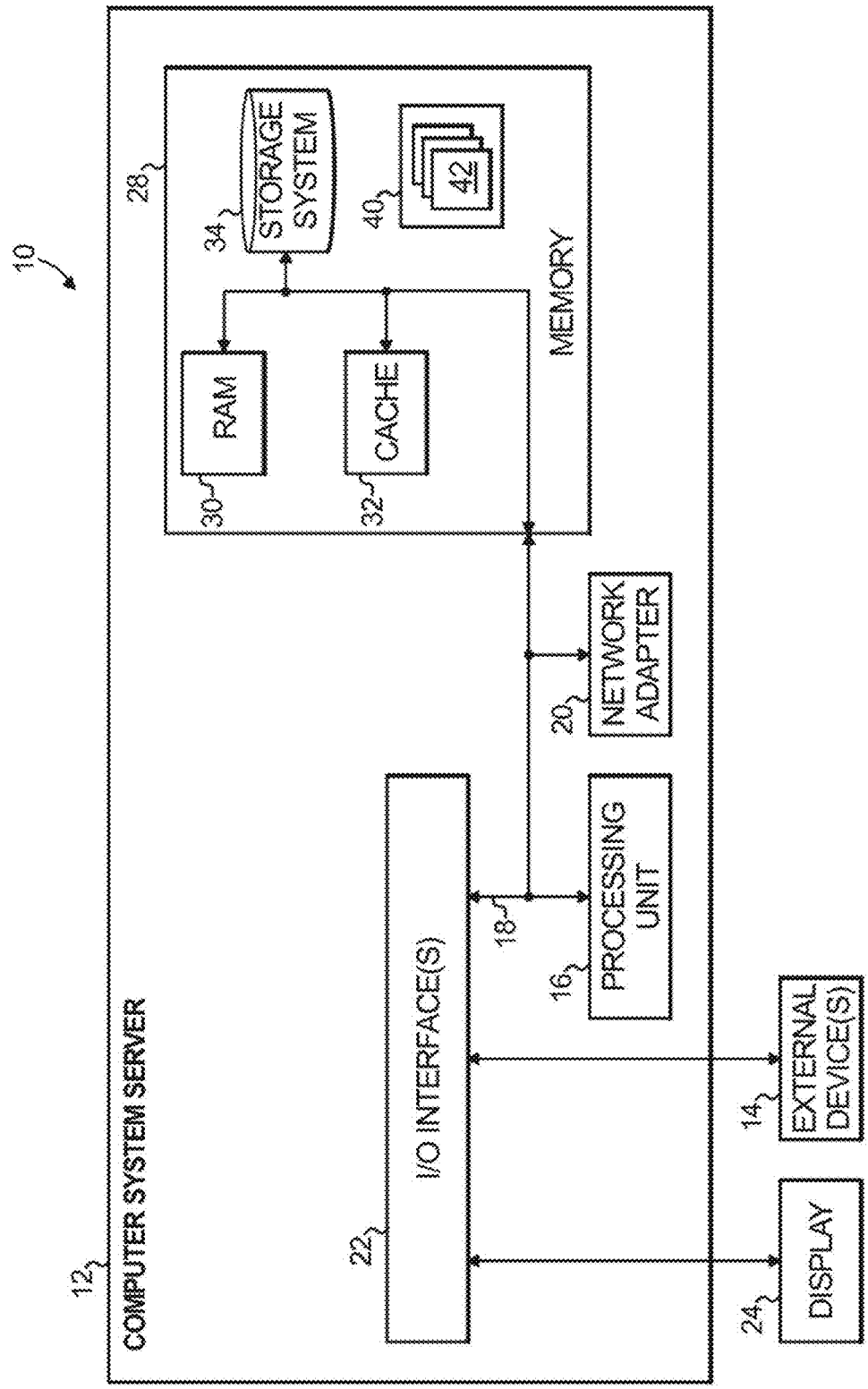
FIG. 14 depicts a computer system that may be useful in implementing one or more aspects and/or elements of the invention, also representative of a cloud computing node according to an embodiment of the present invention.

FIG. 14 depicts a computer system that may be useful in implementing one or more aspects and/or elements of the invention, also representative of a cloud computing node according to an embodiment of the present invention. Referring now to FIG. 14, cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 14, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, and external disk drive arrays, RAID systems, tape drives, and data archival storage systems, etc.

Thus, one or more embodiments can make use of software running on a general purpose computer or workstation. With reference to FIG. 14, such an implementation might employ, for example, a processor 16, a memory 28, and an input/output interface 22 to a display 24 and external device(s) 14 such as a keyboard, a pointing device, a visible light, infrared, or ultraviolet camera, or the like. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory) 30, ROM (read only memory), a fixed memory device (for example, hard drive 34), a removable memory device (for example, diskette), a flash memory and the like. In addition, the phrase "input/output interface" as used herein, is intended to contemplate an interface to, for example, one or more mechanisms for inputting data to the processing unit (for example, mouse), and one or more mechanisms for providing results associated with the processing unit (for example, printer). The processor 16, memory 28, and input/output interface 22 can be interconnected, for example, via bus 18 as part of a data processing unit 12. Suitable interconnections, for example via bus 18, can also be provided to a network interface 20, such as a network card, which can be provided to interface with a computer network, and to a media interface, such as a diskette or CD-ROM drive, which can be provided to interface with suitable media.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 16 coupled directly or indirectly to memory elements 28 through a system bus 18. The memory elements can include local memory employed during actual implementation of the program code, bulk storage, and cache memories 32 which provide temporary storage of at least some program code in order to reduce the number of times code must be retrieved from bulk storage during implementation.

Input/output or I/O devices (including but not limited to keyboards, displays, pointing devices, and the like) can be coupled to the system either directly or through intervening I/O controllers.

Network adapters 20 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 12 as shown in FIG. 14) running a server program. It will be understood that such a physical server may or may not include a display and keyboard.

One or more embodiments can be at least partially implemented in the context of a cloud or virtual machine environment, although this is exemplary and non-limiting. Reference is made back to FIGS. 1-2 and accompanying text.

It should be noted that any of the methods described herein can include an additional step of providing a system comprising distinct software modules embodied on a computer readable storage medium; the modules can include, for example, any or all of the appropriate elements depicted in the block diagrams and/or described herein; by way of example and not limitation, any one, some or all of the modules/blocks and or sub-modules/sub-blocks described. The method steps can then be carried out using the distinct software modules and/or sub-modules of the system, as described above, executing on one or more hardware processors such as 16. Further, a computer program product can include a computer-readable storage medium with code adapted to be implemented to carry out one or more method steps described herein, including the provision of the system with the distinct software modules.

Exemplary System and Article of Manufacture Details

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
   receiving, at a sampling location recommendation module, conventional and complementary information regarding a liquid distribution system, wherein the complementary information includes at least one of a social media post or a consumer report;
   processing the complementary information and a database of the liquid distribution system in the sampling location recommendation module, using computational and artificial intelligence algorithms, to generate a list of locations for sampling the liquid distribution system;
   displaying the list of locations;
   receiving a geo-tagged test record indicative of a sampled contaminant concentration value of at least one location of the list of locations;
   processing the geo-tagged test record, at a contamination source mapping module, to estimate a location and risk of a contamination source in the liquid distribution system; and
   displaying the estimated location and risk of the contamination source by modifying a map of the liquid distribution system,
   wherein processing the geo-tagged test record includes:
   locating the sampled contaminant concentration value on the map of the liquid distribution system by parsing sample coordinates from the geo-tagged test record;
   identifying sampled sections of the liquid distribution system based on a shortest path from a section nearest the sample coordinates; and
   determining a probability that the source of contamination is in the sampled sections using hydraulic modeling of the sampled sections and statistical methods.

2. The method of claim 1, further comprising producing the geo-tagged test record by operation of a microfluidic device capable of performing rapid chemical tests.

3. The method of claim 2, wherein the microfluidic device is a paper-based analytical device.

4. The method of claim 2, further comprising obtaining a result from the microfluidic device via a colorimetric output.

5. The method of claim 4, further comprising:
   generating the geo-tagged test record by capturing and interpreting the colorimetric output from the microfluidic device via a mobile device application; and
   transferring the geo-tagged test record to a cloud application via the mobile device application.

6. The method of claim 2, further comprising obtaining a result from the microfluidic device via an ultraviolet excitation signal.

7. The method of claim 6, further comprising:
   generating the geo-tagged test record by capturing and interpreting a fluorescent signal output produced by the microfluidic device in response to the ultraviolet excitation signal, using a mobile device application; and
   transferring the geo-tagged test record to a cloud application via the mobile device application.

8. The method of claim 2, wherein the microfluidic device carries out chemical tests including an assay for at least one of pH, aluminum, nickel, magnesium, calcium, phosphorus, potassium, copper, lead, mercury, or antimony.

9. The method of claim 1, wherein the computational and artificial intelligence algorithms include at least one of natural language processing, image and video processing, crowdsensing data processing, computational fluid dynamics, optimization routines and statistics.

10. The method of claim 1, further comprising:
    activating an audible, visible, or electronic alert to bring attention to the risk of the contamination source;
    issuing a paper or electronic communication recommending further testing locations; and
    issuing a paper or electronic communication recommending suspension of water distribution to a section suspected of contamination.

11. A non-transitory computer readable medium embodying computer executable instructions which when executed by a computer cause the computer to facilitate:
    receiving, at a sampling location recommendation module, conventional and complementary information regarding a liquid distribution system, wherein the complementary information includes at least one of a social media post or a consumer report;

processing the complementary information and a map of the liquid distribution system in the sampling location recommendation module, using computational and artificial intelligence algorithms, to generate a list of locations for sampling the liquid distribution system;

displaying the list of locations;

receiving a geo-tagged test record indicative of a sampled contaminant concentration value of at least one location of the list of locations;

processing the geo-tagged test record, at a contamination source mapping module, by locating the sampled contaminant concentration value on the map of the liquid distribution system by parsing sample coordinates from the geo-tagged test record, identifying sampled sections of the liquid distribution system based on a shortest path from a section nearest the sample coordinates, and using hydraulic modeling of the liquid distribution system and statistical methods to estimate a location and a risk of a contamination source in the liquid distribution system; and displaying the estimated location and risk of the contamination source by modifying a map of the liquid distribution system.

12. The computer readable medium of claim 11, wherein the computer executable instructions include additional instructions for causing the computer to facilitate:

generating the geo-tagged test record by capturing and interpreting a colorimetric output from a microfluidic device via a mobile device application; and transferring the geo-tagged test record to a cloud application via the mobile device application.

13. The computer readable medium of claim 11, wherein the computer executable instructions include additional instructions for causing the computer to facilitate:

generating the geo-tagged test record by capturing and interpreting a fluorescence signal output from a microfluidic device, via a mobile device application; and transferring the geo-tagged test record to a cloud application via the mobile device application.

14. The computer readable medium of claim 11, wherein the computer executable instructions include additional instructions for causing the computer to facilitate:

activating an audible, visible, or electronic alert to bring attention to the risk of the contamination source;

issuing a paper or electronic communication recommending further testing locations; and issuing a paper or electronic communication recommending suspension of water distribution to a section suspected of contamination.

15. An apparatus comprising:

a memory embodying computer executable instructions; and at least one processor, coupled to the memory, and operative by the computer executable instructions to facilitate:

receiving, at a sampling location recommendation module, conventional and complementary information regarding a liquid distribution system, wherein the complementary information includes at least one of a social media post or a consumer report;

processing the complementary information and a map of the liquid distribution system in the sampling location recommendation module, using computational and artificial intelligence algorithms, to generate a list of locations for sampling the liquid distribution system;

displaying the list of locations;

receiving a geo-tagged test record indicative of a sampled contaminant concentration value of at least one location of the list of locations;

processing the geo-tagged test record, at a contamination source mapping module, by locating the sampled contaminant concentration value on the map of the liquid distribution system by parsing sample coordinates from the geo-tagged test record, identifying sampled sections of the liquid distribution system based on a shortest path from a section nearest the sample coordinates, and using hydraulic modeling of the liquid distribution system and statistical methods to estimate a location and a risk of a contamination source in the liquid distribution system; and displaying the estimated location and risk of the contamination source by modifying a map of the liquid distribution system.

16. The apparatus of claim 15, wherein the computer executable instructions include additional instructions for causing the processor to facilitate:

activating an audible, visible, or electronic alert to bring attention to the risk of the contamination source;

issuing a paper or electronic communication recommending further testing locations; and issuing a paper or electronic communication recommending suspension of water distribution to a section suspected of contamination.

17. The apparatus of claim 15, wherein the computer executable instructions include additional instructions for causing the processor to facilitate:

generating the geo-tagged test record by capturing and interpreting a fluorescence signal output from a microfluidic device, via a mobile device application; and transferring the geo-tagged test record to a cloud application via the mobile device application.

18. The apparatus of claim 15, wherein the computer executable instructions include additional instructions for causing the processor to facilitate:

generating the geo-tagged test record by capturing and interpreting a colorimetric output from a microfluidic device via a mobile device application; and transferring the geo-tagged test record to a cloud application via the mobile device application.

19. The apparatus of claim 15, further comprising:

a microfluidic device capable of carrying out a rapid chemical test and displaying an output based on a result of the test; and a mobile device with an input interface for detecting the output of the microfluidic device, the mobile device being configured to implement a mobile application that generates the geo-tagged test record by capturing and interpreting the output of the microfluidic device and combining the output of the microfluidic device with a location of the mobile device.

* * * * *